United States Patent [19]

Vachy

[11] Patent Number: 5,487,893
[45] Date of Patent: Jan. 30, 1996

[54] ANTIVIRAL USE OF A 2,6-DI-T-BUTYLPHENOL COMPOUND SUBSTITUTED IN 4 POSITION AGAINST HERPES VIRUSES AND PAPILLOMAVIRUSES

[75] Inventor: Robert Vachy, Paris, France

[73] Assignee: Fileco, Paris, France

[21] Appl. No.: 50,279

[22] PCT Filed: Nov. 12, 1991

[86] PCT No.: PCT/FR91/00882

§ 371 Date: Aug. 2, 1993

§ 102(e) Date: Aug. 2, 1993

[87] PCT Pub. No.: WO92/08450

PCT Pub. Date: May 29, 1992

[30] Foreign Application Priority Data

Nov. 12, 1990 [FR] France .................................. 90 13984
Feb. 20, 1991 [FR] France .................................. 91 02028

[51] Int. Cl.$^6$ ........................ A61K 35/78; A61K 31/235; A61K 31/19; A61K 31/11; A61K 31/05
[52] U.S. Cl. ........................ 424/195.1; 514/544; 514/568; 514/699; 514/731
[58] Field of Search .................................. 514/567, 699, 514/720, 731, 647, 733, 568, 544; 424/195.1

[56] References Cited

U.S. PATENT DOCUMENTS 3,974,223 8/1976 Cahoy .................................. 260/600 R
4,708,966 11/1987 Loomans et al. ..

FOREIGN PATENT DOCUMENTS 0061508 10/1982 European Pat. Off. ..
0392077 8/1990 European Pat. Off. ..
2507891 12/1982 France .
2200113 7/1988 United Kingdom .
WO91/13626 9/1991 WIPO .

OTHER PUBLICATIONS

Snipes et al 92 CA:221x 1980.
Hendler et al 114 CA:240608j 1991.
Keith et al. 97 CA:49354k 1982.
Keith 99 CA:181485z 1983.
Hoeua 78 CA:71674u 1973.
Harper et al 78 CA 71675v 1973.
Dacre, J. C., "The metabolism of 3:5–Di–tert.–butyl–4–hydroxytoluene and 3:5–Di–tert.–butyl–4–hydroxybenzoic acid in the rabbit", *Biochem. J.* 78:758–766 (1961).
Grogan, M. W., "Toxicity from BHT ingestion", *West. J. Med* 145:245–246 (1986).
Konovalova, N. P., "Structure and antileukemic actino of a series of substituted phenols", *Pharmacodynamics* 65:9522 (1966).
Llaurodo, J. G., "Beware of phenolic antitoxidants (BHT and BHA)", *West. J. Med* 139:229–230 (1983).
Marinescu, I., "Viral infectious disease treatment by giving alcoholic propolis solution by mouth and painting over locally with alcoholic propolis solution", *Derwent* 83–762896 (1983).
Moffett, Robert, et al., "Central nervous system depressants—III. 2– and 4–Allyloxy–3,5–Disubstituted benzoic acids and derivatives", *J. Med. and Pharm. Chem.* 2:213–227 (1960).
Richards, James T. et al., "Topical butylated hydroxytoluene treatment of genital herpes simplex virus infections of guinea pigs", *Antiviral Research* 5:281–290 (1985).
Shlian, D. M. "Toxicity of butylated hydroxytoluene", *N. Engl. J. Med.* 314:648–649 (1986).
Snipes, W. et al., "Butylated hydroxytoluene inactivates lipid–containing viruses", *Science* 188:64–65 (1975).
Snipes, W. et al., "Hydrophobic alcohols and Di–tert–butyl phenols as antiviral agents", *Symposium on the Pharmacological Effects of Lipids (The American Oil Chemist's Society)* pp. 63–73 (1978).
Szatloczky, E. et al., "Wart removing cosmetic compositions from greater celandine extract and additives in alcohol", *Derwent* 86–313850 (1986).
Tikhonov, A. I. et al., "Physicochemical, microbiologic and quantitative determination of watersoluble polyphenolic preparations of propolis", *Farm.Zh,* 30:42–48 (1975); and.
Yohe, G. R., "The oxidation of 2,6–Di–tert–butyl–4–methylphenol", *J. Org. Chem* 21:1289–1292 (1956).

*Primary Examiner*—Raymond Henley, III
*Attorney, Agent, or Firm*—Weiser & Associates

[57] ABSTRACT

A therapeutical use is provided for compounds selected from the group which consists of (a) phenols of formula (I):

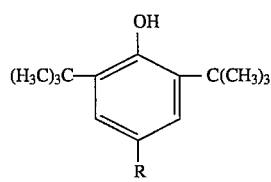

wherein R is a C1–12 alkyl group, a C2–12 alkenyl group, a C2–12 alkynyl group, a C1–12 alkoxy group, a formyl group, a C2–12 alkanoyl group, a C1–12 hydroxyalkyl group, a primary, secondary or tertiary amide group, an OCH$_3$ group, CH$_2$OH or a COOH group or an A—COOH group where A is a C1–11 aliphatic hydrocarbon residue; and (b) the corresponding salts and esters thereof when R is COOH or A—COOH; for obtaining an antiviral drug for use in the human or veterinary therapeutical treatment of viral diseases.

16 Claims, No Drawings

ANTIVIRAL USE OF A 2,6-DI-T-BUTYLPHENOL COMPOUND SUBSTITUTED IN 4 POSITION AGAINST HERPES VIRUSES AND PAPILLOMAVIRUSES

This application is a 371 of PCT/FR91/00882, filed Nov. 12, 1991.

The present invention relates to a new antiviral use of compounds having Formula I below, belonging to the family of 2-6-di-t-butylphenol compounds substituted in the 4 position (alternate nomenclature: 3,5-di-t-butyl-4-hydroxybenzenes substituted in the i position), and resulting in a general manner from the oxidation of 2,6-di-t-butyl-4-methylphenol (alternate nomenclature: 3,5-di-t-butyl-4-hydroxytoluene, or 2,6-di-t-butyl-p-cresol).

This new antiviral use notably manifests itself against lipid-capsid viruses such as the herpes viruses, but also against other viruses, notably papillomaviruses.

It is known that 2,6-di-t-butyl-4-methylphenol (abbreviated HG1) possesses antiviral properties against the herpes viruses such as $HSV_1$, which are lipid-capsid viruses (abbreviated LCV), notably from French Patent Fr. Pat. 2,507,891; from the article of W. SNIPES et al., Sciences, 187, PP. 64–65 (1975), and the article of W. SNIPES et al., entitled "Hydrophobic Alcohols and Di-tert-butyl Phenols as Antiviral Agents" and published in the work "Symposium on the Pharmacological Effects of Lipids," pp. 63–73, The American Oil Chemists' Society, Champaign, Ill. (1978).

In particular it is known that the antiviral properties of 2,6-di-t-butyl-4-methylphenol are so weak against herpes viruses that it is worthwhile to associate it with an adjuvant to enhance these properties (see the aforesaid Fr. Pat. 2,507,891) or to obtain a synergism with propolis (to this end see French Patent Application No. 90 03 093 of 12 Mar. 1992, by the Applicant).

The aforementioned French Application No. 90 03 093 more specifically recommends a synergistic association of a phenol component belonging to the set of 2,6-di-t-butylphenols (abbreviated BHT, i.e., compounds having Formula I where R is an aliphatic hydrocarbon group with $C_1$-$C_{12}$), with propolis in accordance with a BHT-to-propolis ratio by weight of from 100:1 to 650:1, and better from 135:1 to 560:1, for the treatment of infections caused by LCVs.

It is furthermore known-that compounds having Formula I below, where R is an oxygen residue, have already been described or seriously proposed as oxidation products of BHT compounds (notably HG1) or as metabolites of BHT compounds (notably HG1). To this end see the articles of G.R. YOHE et al., J. Org. Chem. 21, pp. 1289–1292 (1956), T. H. COFFIELD et al., J. Am. Chem. Soc. 79, 5019–5023 (1957), J. C. DACRE, Biochem. J. 78, pp. 758–766 (1961), and M. AKAGI et al., Chem. Pharm. Bull. (Tokyo) 10, pp. 101–105 and 200–204 (1962).

One finds that after oral or even injectable administration of HG1, in vivo metabolization into compounds having Formula I, where R is a residue containing oxygen such as $CH_2OH$, $OCH_3$ or COOH, is slow and happens late. Consequently the quantities of biologically formed metabolites available in the organism, which are not eliminated by natural routes, are to the Applicant's knowledge insufficient to produce the beneficial antiviral effects, notably against LCVs such as the herpes viruses, on the one hand, and papillomaviruses, on the other hand.

Moreover, in the local administration of HG1 on the skin, in the case of treatment of skin conditions caused by herpes viruses, the metabolization of HG1 into compounds having Formula I, where R is $CH_2OH$, $OCH_3$ or COOH, does not take place. This explains why after local administration of HG1, the beneficial antiviral properties of compounds having Formula I, where R is $OCH_3$, $CH_2OH$ or COOH, have never been able to manifest themselves.

Finally, it is known that 3,5-di-t-butyl-4-hydroxybenzoic acid, which is a compound having Formula I where R is COOH, has been used as an intermediate product in synthesis (see in particular Example 1 of EP-A-0 269 981) and that the halogenides of this acid, notably the bromide and chloride, have also been used as intermediate products in synthesis (see the aforementioned EP-A-0 269 981, and U.S. Pat. No. 4,708,966).

PURPOSE OF THE INVENTION

It has surprisingly just been found that the compounds having Formula I are of particular benefit as antiviral agents, in view of their inhibiting (i.e., virustatic) and/or virulicidal (i.e., virucidal) effects on viruses, particularly against lipid-capsid viruses (abbreviated LCV), such as the herpes viruses, but also against other viruses and notably papillomaviruses.

In accordance with a first aspect of the invention, it is proposed to provide a new use of the compounds having Formula I, as antiviral agents.

In accordance with a second aspect of the invention, it is proposed to provide an antiviral therapeutic composition containing at least one compound having Formula I.

In accordance with a third aspect of the invention, it is proposed to provide a new method for the preparation of said compounds having Formula I.

OBJECT OF THE INVENTION

More specifically, in accordance with the invention, a new therapeutic use is proposed, characterized in that it involves a 2,6-di-t-butylphenol. compound substituted in the 4 position (alternate nomenclature: 3,5-di-t-butyl-4-hydroxybenzene substituted in the 1 position) chosen from among the set consisting of:

(a) The phenols having the formula

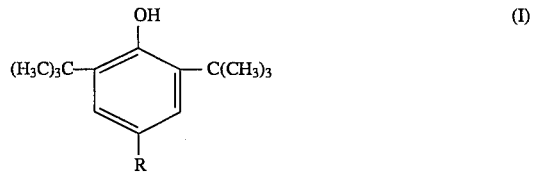

where R is an alkyl group with $C_1$-$C_{12}$, an alkenyl group with $C_2$-$C_{12}$, an alkynyl group with $C_2$-$C_{12}$, an alkoxy group with $C_1$-$C_{12}$, a formyl group, an alkanoyl group with $C_2$-$C_{12}$, a hydroxyalkyl group with $C_1$-$C_{12}$, a primary, secondary or tertiary amide group, an $OCH_3$, $CH_2OH$, CHO or COOH group, or an A-COOH group where A is an aliphatic hydrocarbon residue with $C_1$-$C_{11}$, and (b) Their corresponding salts and esters when R is COOH or A—COOH for the obtainment of an antiviral medication intended for use in human or veterinary therapy against diseases caused by viruses.

This use is notably appropriate for the local treatment of skin diseases or infections caused by said viruses.

More specifically, the invention proposes the antiviral use of the following substituted phenol compounds:
3,5-di-t-butyl-4-hydroxybenzoic acid,
3,5-di-t-butyl-4-hydroxyanisole
3,5-di-t-butyl-4-hydroxyphenylmethanol
3,5-di-t-butyl-4-hydroxybenzaldehyde.

Under the invention, an antiviral composition is also recommended, characterized in that it includes, in association with a physiologically acceptable excipient, at least one compound having Formula I.

Obviously such a composition will include a therapeutically active quantity of antiviral compound having Formula I.

The compounds having Formula I, in which R is $OCH_3$, $CH_2OH$, CHO or LOOH [sic], and the corresponding salts and esters when R is COOH, are particularly useful as antiviral substances against infections caused by LCVs such as, notably, the herpes viruses $HSV_1$, $HSV_2$ and $HSV_1R$.

Thus the invention proposes to provide a new use of the compounds having Formula I, cited above, to obtain an antiviral medication intended for use in therapy against diseases caused by lipid-capsid viruses, and more specifically the herpes viruses.

The compounds having Formula I, in which R is $OCH_3$, $CH_2OH$, CHO or LOOH [sic], and the corresponding salts and esters when R is COOH, may be prepared by a method known in itself, applying classic reaction mechanisms. The process recommended under the invention consists in reacting a 2,4-di-t-butyl- 4-halogen phenol (alternate nomenclature: 3,5-di-t-butyl- 4-hydroxy-halogenobenzene) having the formula

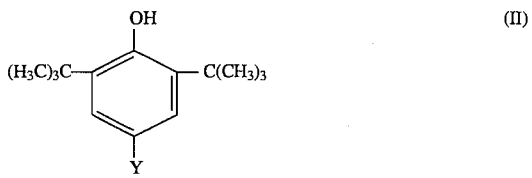

where Y is a halogen atom, preferably Br or Cl, with a compound having the formula

where R' is $OCH_3$, $CH_2OH$, CHO, COOH, COOX or COZ, where X is $NH_4^+$ or $1/mM^{m+}$, where M represents a metal from the groups Ia, Ib, IIa and IIb of the periodic table, and m is its valence, and where Z is an alkyl or aminoalkyl residue, where each alkyl group has $C_1$-$C_5$, in the presence of an alkaline metal, alkaline metal hydroxide or alkaline hydride.

In the implementation of this process, if necessary the OH group of the phenol function will be protected in a manner known in itself, notably by replacing said phenol OH group with an $OSi(CH_3)_3$ group on the one hand, and likewise the OH groups of $R'=CH_2OH$ or COOH will be protected in a manner known in itself, on the other hand.

The papillomaviruses, which are viruses without a lipid capsid or capsule, and which therefore are not among the set of so-called lipid-capsid viruses, cause viral infections that are manifested by condylomas. In particular, human papillomaviruses (abbreviated HPV) are responsible for ano-genital condylomas, which are sexually transmitted diseases.

It is known that flat or acuminate condylomas due to HPVs are very common, and that the therapies recommended for their treatment are (i) limited; (ii) not always effective and (iii) not sufficiently well tolerated.

Among these known therapies, it is known that those involving physical methods are either more or less painful (electrocoagulation, cryotherapy), or expensive ($CO_2$ laser), and in practice all require anesthesia; and those involving anti-condyloma chemical agents of reference, such as podophyllin, podophyllotoxin and fluorouracil (i.e., 5-fluoro-2,4-(1H,3H)-pyrimidinedione), are often irritating and potentially toxic.

Moreover, whatever the treatment employed, these known therapies still present the drawback that the recidivism rate is always high because of recontamination or latent viral infection. The invention proposes to provide a new technical solution for the treatment of condylomas caused by papillomaviruses, making it possible to alleviate the above-listed drawbacks of the previously known therapeutic solutions.

In fact it has been found, surprisingly, that the compounds having Formula I in which R is:

an alkyl group with $C_1$-$C_{12}$, an alkenyl group with $C_2$-$C_{12}$, an alkynyl group with $C_2$-$C_{12}$, an alkoxy group with $C_1$-$C_{12}$, a formyl group, an alkanoyl group with $C_2$-$C_{12}$, a hydroxyalkyl group with $C_1$-$C_{12}$, a COOH group, or an A—COOH group where A is an aliphatic hydrocarbon residue with $C_1$-$C_{11}$, and Their corresponding salts and esters when R is COOH or A—COOH, are particularly useful as anti-papillomaviral substances when used against condylomas induced by papillomaviruses, and in particularly condylomas of the uro-genital system, notably ano-genital condylomas due to HPVs.

Thus the invention proposes to provide a new use of the above-mentioned compounds having Formula I, to obtain an anti-papillomaviral medication intended for use in therapy against condylomas caused by papillomaviruses.

This use is notably appropriate for the local treatment of ano-genital condylomas caused by said papillomaviruses.

Also recommended under the invention is an anti-papillomaviral composition characterized in that it includes, in association with a physiologically acceptable excipient, at least one compound having Formula I above.

Naturally, such a composition will include a therapeutically active quantity of anti-papillomaviral component having Formula I.

More specifically the invention proposes the anti-papillomaviral use of the compounds having Formula I, in which R is chosen from among the set consisting of the following groups: methyl, ethyl, propyl, isopropyl, butyl, isobutyl, s-butyl, t-butyl, amyl, isoamyl, 2,2-dimethylpropyl, n-hexyl, 1,1,3,3-tetramethylbutyl and decyl, $CH_2OH$, CHO, COOH, methyloxy, ethyloxy, propyloxy, isopropyloxy, butyloxy, isobutyloxy, s-butyloxy, t-butyloxy, amyloxy, isoamyloxy, 2,2-dimethylpropyloxy, n-hexyloxy, 1,1,3,3-tetramethylbutyloxy and decyloxy.

And more specifically, those in which R is chosen from among the set consisting of $OCH_3$, $CH_2OH$, COOH, $CH_3$, n-$C_4H_9$, t-$C_4H_9$, n-$C_6H_{13}$, $CH_2C(CH_3)_3$ and $C(CH_3)_2$—$CH_2$—$C(CH_3)_3$.

ABBREVIATIONS

For convenience's sake, the following abbreviations have been used in the present description.

Ala=alanine

Arg=arginine

BG1=3,5-di-t-butyl-4-hydroxyanisole, a compound having Formula I where R is $OCH_3$ (alternate nomenclature: 2,6-di-t-butyl-4-methoxyphenol)

BG2=3,5-di-t-butyl-4-hydroxyphenylmethanol, a compound having Formula I where R is $CH_2OH$ (alternate nomenclature: 3,5-di-t-butyl-4-hydroxybenzyl alcohol, or 2,6-di-t-butyl-4-hydroxymethylphenol)

BG3=3,5-di-t-butyl-4-hydroxybenzaldehyde, a compound having Formula I where R is CHO (alternate nomenclature: 2,6-di-t-butyl-4-formylphenol)

BG4=3,5-di-t-butyl-4-hydroxybenzoic acid, a compound having Formula I where R is COOH (alternate nomenclature: 4-carboxy-2,6-di-t-butylphenol)

BHT=2,6-di-t-butylphenol Compound having Formula I where R is an aliphatic hydrocarbon residue (the letters BHT historically derive from the English expression "butylated hydroxytoluene")

Glu=Glutamic acid $DI_{50}$=Infectious dose 50 (i.e., dose inducing a viral infection in 50% of animals (adult male mice) receiving the test virus))

EBV=Epstein-Barr virus

Gly=Glycine

HG1=2,6-di-t-butylparacresol (i.e., BHT having Formula I in which R is methyl)

HG4=2,6-di-t-butyl-4-butylphenol (i.e., BHT having Formula I in which R is n-butyl)

HGt4=2,4,6-tri-t-butylphenol (i.e., BHT having Formula I in which R is t-butyl)

HGt5=2,6-di-t-butyl-4-(2,2-dimethylpropyl)phenol (i.e., BHT having Formula I in which R is $CH_2C(CH_3)_3$)

HG6=2,6-di-t-butyl-4-hexylphenol (i.e., BHT having Formula I in which R is n-hexyl)

HGt8=2,6-di-t-butyl-4- (1,1,3,3-tetramethylbutyl) phenol (i.e., BHT having Formula I in which R is C $(CH_3)_2$-$CH_2$—$C(CH_3)_3$)

His=Histidine

HPV=Human papillomavirus $HSV_1$=Herpes simplex virus type 1

$HSV_2$=Herpes simplex virus type 2

$HSV_1R$=Acyclovir-resistant herpes simplex virus type 1 (acyclovir=antiviral substance of reference corresponding to the developed formula 2-amino- 1,9-dihydro-9-[(2-hydroxyethoxy)methyl]-6H-purine- 6-one)

3Hyp=3-hydroxyproline

4Hyp=4-hydroxyproline

Ile=Isoleucine

LCV=Lipid-capsid virus

Leu=Leucine

Lys=Lysine

MeGly=Methyl glycine (i.e., sarcosine)

Nle=Norleucine

Nva=Norvaline

Orn=Ornithine

TV=Infectious titer with regard to test virus specimen; here this titer is a multiple of $DI_{50}$/ml ZV=Zoster virus Phe=Phenylalanine Pro=Proline Prp=Propolis $R_p$=Ratio by weight (from French "rapport pondéral")

RT=Ambient temperature (15°–20° C.)

Val=Valine

DETAILED DESCRIPTION OF THE INVENTION

The compounds having Formula I of the invention contain a group R which is an aliphatic hydrocarbon residue, with or without oxygen, having a linear or branched hydrocarbon chain with $C_1$-$C_{12}$.

When R is a non-oxygenated aliphatic residue it may represent an alkyl, alkenyl or alkynyl group having no more than 12 atoms of carbon. Among the appropriate alkyl groups with $C_1$-$C_{12}$ one might notably mention the following: methyl, ethyl, propyl, isopropyl, butyl, isobutyl, s-butyl, t-butyl, amyl, isoamyl, 2,2-dimethylpropyl, n-hexyl, 1,1,3, 3-tetramethylbutyl and decyl. Among the appropriate $C_2$-$C_{12}$ alkenyl groups one might notably mention the following: —CH=$CH_2$, —CH=CH—$CH_3$, —$CH_2$—CH=$C_2$, —$C(CH_3)_2$—CH=CH—$CH_3$, —CH=CH—CH=$CH_2$, —$C(CH_3)$=CH—CH=$CH_2$ and —$CH_3$—CH=CH—$CH_3$. Among the appropriate $C_2$-$C_{12}$ alkynyl groups one might notably mention the following: —C≡CH, —$CH_2$—C≡CH, —$CH_2$—C≡C—$CH_3$ and —$CH(CH_3)$—C≡C—$CH_3$, When R is an oxygenated aliphatic residue with $C_1$-$C_{12}$, it may have one or more ether, carbonyl, hydroxyl or carboxyl functions. Among the appropriate R=alkoxy groups with $C_1$-$C_{12}$ one might notably mention the following: methyloxy, ethyloxy, propyloxy, isopropyloxy, butyloxy, isobutyloxy, s-butyloxy, t-butyloxy, amyloxy, isoamyloxy, 2,2-dimethylpropyloxy, n-hexyloxy, 1,1,3,3-tetramethylbutyloxy and decyloxy. Among the appropriate R groups with $C_1$-$C_{12}$ having a carbonyl function CO one might notably mention the following: —CHO, —$COCH_3$, —$COCH_2CH_3$, —$COCH_2CH_2CH_3$, —$COCH(CH_3)_2$, —$COC(CH_3)_3$, —$COCH_2CH_2CH_2CH_3$ and $COC(CH_3)_2CH_2(CH_3)_3$. Among the appropriate R groups with $C_1$-$C_{12}$ having a hydroxyl function OH one might notably mention the omega-hydroxylated groups: 13 $CH_2OH$, —$CH_2CH_2OH$, —$CH_2CH_2CH_2OH$, —$C(CH_3)_2OH$, —$C(CH_3)_2CH_2OH$, —$CH_2C(CH_3)_2OH$, —$CH_2C(CH_3)_2CH_2OH$, —$CH_2CH_2CH_2CH_2OH$, $CH(CH_3)CH_2CH(CH_3)OH$ and —$C(CH_3)_2CH_2C(CH_3)_2CH_2OH$. Among the appropriate R groups with $C_1$-$C_{12}$ having an omega-carboxyl function one might notably mention the —COOH and —A—COOH groups in which A is an aliphatic hydrocarbon residue with $C_1$-$C_{11}$, such as —COOH, —$CH_2COOH$, —$CH(CH_3)COOH$, —$C(CH_3)_2COOH$, —$CH_2CH_2CH_2COOH$, —$CH(CH_3)_2CH_2COOH$, —CH=CH—COOH and —$C(CH_3)$=$C(CH_3)$—COOH.

Without departing from the scope of the invention, the oxygenated aliphatic group R may have (i) at its end linked to the phenol residue, an ether —O— or carbonyl —CO— function, and (ii) at its other end, an omega—OH or omega—COOH function, with the two ends being linked together by a linear or branched hydrocarbon chain such that the total number of carbon atoms in R is no more than 12.

Among the appropriate salts of the compounds having Formula I, where R is COOH or A—COOH, one might notably mention the mineral salts obtained by the reaction of the acid having Formula I where R=COOH or A—COOH with a mineral base. These mineral salts are the compounds having Formula I in which R=COOX, where X represents $NH_4^+$ cation 1/mM$^{m+}$, M is a metal from the groups Ia, Ib, IIa and IIb of the periodic table, and m is its valence, notably $Na^+$, $K^+$, ½$Ca^{2+}$, ½$Zn^{2+}$, ½$Mg^{2+}$, $CU^+$ or ½$Cu^{2+}$.

One might also mention the addition salts obtained by reacting a compound having Formula I where R=COOH or A—COOH with an organic base, such as notably the alkylamines and dialkylamines (where each alkyl fragment is a $C_1$-$C_8$ radical with a linear or branched hydrocarbon chain), the N-hydroxyalkylamines in which the alkyl fragment is a divalent $C_1$-$C_8$ radical with a linear or branched hydrocarbon chain, such as 2-hydroxyethylamine); the single-ring saturated or unsaturated cyclic amines (e.g., pyridine, 3-methylpyridine, pyrrolidine, piperidine, 4-methylpiperidine, morpholine, thiomorpholine, piperazine, 4-methylpiperazine, 4-phenylpiperazine, 4-(4-chlorophenyl)piperazine, 4-(2hydroxyethyl)piperazine and hexamethyleneimine), and the amino acids (e.g., Arg, His, Orn, Lys, Gly, Ala, Phe, Glu, Leu, Ile, Nle, Val, Nva, MeGly, Pro, 4Hyp or 3Hyp, where each acid function of the said amino acids is capable of being blocked by a known method of peptide synthesis).

The esters of the acid compounds having Formula I where R is COOH or A—COOH may be represented by the formulas COOZ or A—COOZ, where A is defined as above and Z is a hydrocarbon residue capable of being aminated. Advantageously, Z will include an aliphatic hydrocarbon residue with $C_1$-$C_5$, and the amino group it may contain will be $NH_2$, or one of the following groups: monoalkylamino, dialkylamino, N-hydroxyalkylamino and cyclic amino, as defined in the context of the addition salts above.

Among the appropriate esters of acid components having Formula I where R is COOH or A—COOH, one might notably mention the alkyl and aminoalkyl esters in which each alkyl fragment is a linear or branched hydrocarbon residue with $C_1$-$C_5$.

Generally, acid BG4 (Formula I, R=COOH) is preferred over the salts and esters. In fact it has been found that said salts and esters act less rapidly than the corresponding acid, in the sense that after administration they delay the splitting off of the active acid form BG4.

For the same reason, the R=A—COOH acids are preferred over the corresponding salts and esters. Furthermore, it has been possible to determine that the acid BG4 (compound having Formula I in which R=COOH) is more effective as an anti-papillomaviral agent than are the acids having Formula I in which R is A—COOH.

The antiviral compounds of the invention thus include BG1, BG2, BG3, BG4 as well as the salts and esters of BG4.

Among the appropriate salts of BG4 one might notably mention the mineral salts obtained by reacting the acid having Formula I where R=COOH with a mineral base. These mineral salts are compounds having Formula I in which R=COOX, with X representing $NH_4^+$ or a cation $1/mM^{m+}$, where M is a metal of the groups Ia, Ib, IIa and IIb of the periodic table and m is its valence, notably $Na^+$, $K^+$, ½$Ca^{2+}$, ½$Zn^{2+}$, ½$Mg^{2+}$, $CU^+$ or ½$Cu^{2+}$.

One might also mention the addition salts obtained by reacting BG4 with an organic base, such as notably the alkylamines and dialkylamines (where each alkyl fragment is a $C_1$-$C_8$ radical with a linear or branched hydrocarbon chain), the N-hydroxyalkylamines where the alkyl fragment is a divalent radical with $C_1$-$C_8$ having a linear or branched hydrocarbon chain, such as 2-hydroxyethylamine); the single-ring saturated or unsaturated cyclic amines (e.g., pyridine, 3-methylpyridine, pyrrolidine, piperidine, 4-methylpiperidine, morpholine, thiomorpholine, piperazine, 4-methylpiperazine, 4-phenylpiperazine, 4-(4-chlorophenyl)piperazine, and 4-(2-hydroxyethyl)piperazine and hexamethyleneimine), and the amino acids (e.g., Arg, His, Orn, Lys, Gly, Ala, Phe, Glu, Leu, Ile, Nle, Val, Nva, MeGly, Pro, 4Hyp or 3Hyp).

Among the appropriate BG4 esters, one might notably mention the alkyl and aminoalkyl esters where each alkyl fragment is a linear or branched hydrocarbon residue with $C_1$-$C_5$.

Generally, the acid BG4 is preferred over its salts and esters. It has in fact been found that such salts and esters act less rapidly than the corresponding acid, in the sense that after administration they delay the splitting off of the active acid form BG4.

Table I below presents, in a non-limiting manner, a certain representative number of compounds having Formula I of the invention.

TABLE I $$\underset{R}{\underset{|}{\overset{OH}{\underset{|}{\bigcirc}}}} \quad (I)$$

(with $(H_3C)_3C$— and —$C(CH_3)_3$ substituents ortho to OH)

| Product | Abbreviation or Code | R |
|---|---|---|
| Ex 1 | BG1 | $OCH_3$ |
| Ex 2 | BG2 | $CH_2OH$ |
| Ex 3 | BG3 | CHO |
| Ex 4 | BG4 | COOH |
| Ex 5 | — | COONa |
| Ex 6 | — | COOH, morpholine |
| Ex 7 | — | COOH, $H_2NCH_2CH_2OH$ |
| Ex 8 | — | COOH, pyridine |
| Ex 9 | — | $COOCH(CH_3)_2$ |
| Ex 10 | — | $COOC(CH_3)_3$ |
| Ex 11 | HG1 | $CH_3$ |
| Ex 12 | HG4 | $(CH_2)_3CH_3$ |
| Ex 13 | HGt4 | $C(CH_3)_3$ |
| Ex 14 | HGt5 | $CH_2C(CH_3)_3$ |
| Ex 15 | HG6 | $(CH_2)_5CH_3$ |
| Ex 16 | HGt8 | $C(CH_3)_2CH_2C(CH_3)_3$ |
| Ex 17 | — | $CH=CH_2$ |
| Ex 18 | — | $CH=CH-CH_3$ |
| Ex 19 | — | $C(CH_3)_2CH=CHCH_3$ |
| Ex 20 | — | $C\equiv CH$ |
| Ex 21 | — | $OCH_2CH_3$ |
| Ex 22 | — | $OC(CH_3)_3$ |
| Ex 23 | — | $OCH_2C(CH_3)_3$ |
| Ex 24 | — | $OC(CH_3)_2CH_2C(CH_3)_3$ |
| Ex 25 | — | $COCH_3$ |
| Ex 26 | — | $COCH_2CH_3$ |
| Ex 27 | — | $COCH(CH_3)_2$ |
| Ex 28 | — | $CH_2CH_2OH$ |
| Ex 29 | — | $CH_2C(CH_3)_2OH$ |
| Ex 30 | — | $C(CH_3)_2CH_2OH$ |
| Ex 31 | — | $CH_2COOH$ |
| Ex 32 | — | $C(CH_3)_2COOH$ |
| Ex 33 | — | $C(CH_3)_2CH_2COOH$ |
| Ex 34 | — | $CH(CH_3)COOH$ |
| Ex 35 | — | $CH_2COOLi$ |
| Ex 36 | — | $C(CH_3)_2COO$—½ $Mg^{2+}$ |
| Ex 37 | — | $OCH_2COOH$ |
| Ex 38 | — | $OC(CH_3)_2COOH$ |
| Ex 39 | — | $COCH_2COOH$ |
| Ex 40 | — | $COCH_2CH_2OH$ |
| Ex 41 | — | $OC(CH_2)_2CH_2OH$ |
| Ex 42 | — | $OCH_2C(CH_3)_2OH$ |
| Ex 43 | — | $OCH=CH-COOH$ |

I. Therapeutic use of compounds having Formula I in which R is $OCH_3$, $CH_2OH$, CHO or COOH and the corresponding salts and esters when R is COOH, to obtain an anti-herpes virus medication These compounds having Formula I of the invention are particularly active as antiviral agents in man and warm-blooded animals, notably mammals, against infections caused by viruses, in particular the vital strains belonging to the LCV group.

The LCV group includes notably EBV, $IV_A$, ZV and the herpes viruses.

These compounds having Formula I are more specifically beneficial against the strains $HSV_1$, $HSV_2$ and $HSV_1R$, since in the treatment of herpes, they can easily be formulated in a lipid excipient for local administration on the skin, of the nature of a lotion, cream, salve or pomade, by virtue of their oleophilic and lipophilic properties.

These compounds having Formula I may, as indicated above, be prepared by a method which is in itself known, notably by the oxidation of BHT to form BG2, BG3 and then BG4.

The process recommended under the invention for the preparation of these compounds having Formula I, and schematized by the following reaction mechanism A:

applies to the synthesis of all these compounds having Formula I. It is advantageously applied by reacting the compounds II and III in an appropriate solvent, at a molar ratio II:III of preferably between 1:1.2 and 1:1.9.

As a variant, BG2 and BG4 may be prepared from BG3 by a procedure schematized by reaction mechanism B:

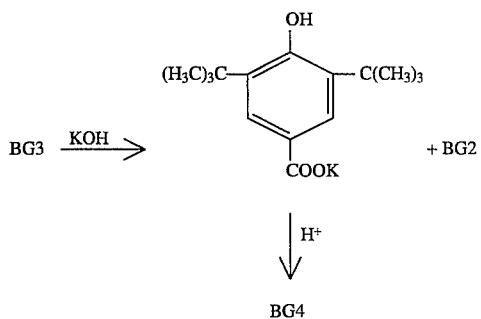

comprising the isolation of BG2 and BG4.

In accordance with reaction mechanism B BG3 is reacted with a strong base (KOH (preferably) or NaOH in a molecular ratio of BG3 to strong base of between 1:1.3 and 1:1.8, in an appropriate solvent (notably an aromatic solvent such as benzene (preferably), toluene or xylene), for at least 1 hour at the reflux temperature of the reaction mixture. After cooling to RT, water is added to solubilize the formed BG4 salt. After decanting, the aqueous phase is extracted with ether. The aqueous and organic phases are separated to isolate BG2 from the organic phase and BG4 from the aqueous phase.

As a variant, one may also prepare BG4, which is the most interesting product of the invention, from BG3 by a process schematized by reaction mechanism C:

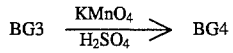

comprising the reaction of BG3 with $KMnO_4$ in the presence of $H_2SO_4$ for at least 2 hours at a temperature of not more than 20° C., with BG4 then being isolated from the reaction medium.

The best method of application under the invention consists in using compound BG4 as an antiviral substance, notably against LCVs and in particular against herpes viruses and more particularly against the strains $HSV_1$, $HSV_2$ and $HSV_1R$.

Other advantages and characteristics of the invention will be better understood from a reading below of sample preparations and comparative trials.

It is understood that the combination of these elements is by no means limiting but is given simply as an illustration.

COMPARATIVE TRIALS

The virulicidal properties of these compounds having Formula I of the invention were assessed in relation to a comparison product A (i.e., BHT). To this end, the infectious titer (TV) of each product to be tested was assessed in relation to the infectious titer ($TV_o$) of a virus specimen ("stock virus" of $HSV_1$ strain); then the $\log(TV/TV_o)$ value was calculated.

Under this protocol, to determine $TV_o$ a composition was used consisting of 0.5 ml of MEM culture medium and 0.5 ml of stock virus, and to determine TV a composition was used consisting of 0.5 ml of product to be tested in the aforesaid MEM medium and 0.5 ml of stock virus. The samples were incubated at 37° C. for 1 hour, centrifuged, and then the $TV_o$ and TV values were measured on a microtitration plate.

The obtained results are listed in Table II below, in which the $TV_o$ and TV values are multiples of the $DI_{50}$/ml.

TABLE II

| | VIRULICIDAL ACTIVITY | |
|---|---|---|
| Product | Infectious Titer ($\times DI_{50}$/ml) | $\log(TV/TV_o)$ |
| Virus | $TV_o = 10^5$ | — |
| Ex 1 (BC1) | $TV = 10^{1,5}$ | −3,5 |
| Ex 2 (BC2) | $TV = 10^{1,5}$ | −3,5 |
| Ex 3 (BC3) | $TV = 10^3$ | −2 |
| Ex 4 (BC4) | $TV = 0$ (a) | −5 (b) |
| A (BHT) | $TV = 10^{3,5}$ | −1,5 |

Notes
(a) Eradication
(b) The $\log(TV/TV_o)$ value is recorded as equal to −5 in view of the aforementioned eradication.

The results in Table II show that the decrease in infectious titer is greatest for BG4 compared to the other products. The activity of the tested products against the $HSV_1$ strain is as follows:

BG4>BG1=BG2>BG3>BHT.

SUPPLEMENTARY TESTS

Supplementary tests were performed with BG4, the most effective product as an anti-viral agent in accordance with the invention. These supplementary tests were undertaken at RT, (i) with a BG4 concentration of 0.1% weight/volume for 1 hour, and (ii) with a BG4 concentration of 0.5% weight/volume for 0.5 hrs.

In the first case, it was found that there was eradication (i.e., total destruction or inhibition of the viruses) in 1 hour at RT, and in the second case, that there was eradication in 0.5 hrs at RT.

The results of other tests performed with increasing doses of BG4 after an incubation with a virus specimen for 1 hour at 37° C., on the one hand., and for 0.5 hour at 37° C., on the other hand, are listed in Table III below, which confirms the aforesaid eradication.

TABLE III

| Dose of BG4 (% weight/volume) | Incubation 1 hr at 37° C. | | Incubation 0.5 hr at 37° C. | |
|---|---|---|---|---|
| virus | $TV_o = 10^5$ | — | $TV_o = 10^5$ | — |
| 5,0 | $TV = 0$(a) | −5(b) | $TV = 0$ | −5(b) |
| 2,5 | $TV = 0$(a) | −5(b) | $TV = 0$ | −5(b) |
| 1,0 | $TV = 0$(a) | −5(b) | $TV = 0$ | −5(b) |
| 0,50 | $TV = 0$(a) | −5(b) | $TV = 0$ | −5(b) |
| 0,25 | $TV = 0$(a) | −5(b) | $TV = 10^1$ | −4 |
| 0,10 | $TV = 0$(a) | −5(b) | $TV = 10^2$ | −3 |

TABLE III-continued

| Dose of BG4 (% weight/volume) | Incubation 1 hr at 37° C. | | Incubation 0.5 hr at 37° C. | |
| --- | --- | --- | --- | --- |
| 0,050 | TV = $10^1$ | −4 | TV = $10^3$ | −2 |
| 0,025 | TV = $10^2$ | −3 | TV = $10^4$ | −1 |
| 0,010 | TV = $10^3$ | −2 | TV = $10^4$ | −1 |

Notes
(*) Infectious titer (× $DI_{50}$/ml)
(**) Log(TV/$TV_o$)
(a) and (b) as in Table II

PREPARATION I - Formulation

A mixture of 59 g of white vaseline, 3 g of sorbitan sesquioleate and 3 g of glycerol monooleate is heated to 70°–75° C. Heating is discontinued when the mixture has become homogeneous, and then 5 g of BG4 are added while agitating. Then 30 g of water are added at a temperature of 65° C. or less and agitation is continued until the mixture cools to RT. It is homogenized and yields a pomade consisting of a water-in-oil emulsion, usable as a collyrium.

PREPARATION II - Formulation

At 70°–75° C. 57 g of white vaseline are mixed with 3.6 g of sorbitan sesquioleate and 3.6 g of glycerol monooleate. When the mixture is homogeneous, heating is discontinued and 5.8 g of HG1 are added. Mixing is resumed and with agitation, 30 g of water are added at a temperature below about 70° C. Agitation is continued until the mixture cools to RT. Then it is homogenized and yields a pomade consisting of a water-in-oil emulsion, usable as a collyrium.

PREPARATION III-Formulation 4.7 g of polyethylene glycol 1500 stearate are mixed with 13 g of glycerol monostearate, 3 g of glycerol monooleate, 10.5 g of decyl oleate, 5.5 g of capric/caprylic triglyceride, and 5 g of glycerol isostearate. The mixture is gradually heated to 70°–75° C. and heating is discontinued as soon as the mixture becomes homogeneous. Then 8 g of BG4 are added and the mixture is agitated slowly. Then 3 g of propylene glycol, 0.3 g of citral and 47 g of water are poured into the resulting mixture. The resulting mixture is agitated while being allowed to cool to RT. After passing through a homogenizer, it yields a water-in-oil emulsion having the consistency of a cream.

PREPARATION IV

Obtainment of BG4 by Reaction Mechanism B a) A balloon flask equipped with a spherical funnel for the introduction of liquid reagent ("spherical dropping funnel") and a cooler is filled with a solution of 10 g (43 mmol) of 3,,5-di-t-butyl-4-hydroxybenzaldehyde (BG3) in 20 ml of benzene. Via the spherical dropping funnel, 6.6 ml of an aqueous solution of KOH at 60% weight/volume (i.e., 3.96 g (71 mmol) of KOH) are added, and the mixture is energetically agitated until a homogeneous emulsion is obtained. The resulting reaction mixture is heated to reflux temperature over night. (i.e., approximately 8–14 hours). After cooling, 15 ml of water are added to solubilize the potassium salt of 3,5-di-t-butyl-4-hydroxybenzoic acid that has formed. After decanting, the aqueous phase is collected, and extracted with diethyl ether (3×15 ml). Then the aqueous phase, on the one hand, and the recombined organic phases, on the other hand (said recombined organic phases will be used in preparation V below) are treated separately.

b) The aqueous phase is agitated with 5 ml of sodium bisulfite, then acidified with HCl diluted to a third. The precipitate that forms is filtered, washed to neutral, dried in the oven at 75° C., then purified on a silica gel column using a diethyl ether/petroleum ether 30/70 v/v mixture as eluent. One obtains 3.33 g (yield: 62.4%) of the expected product, 3,5-di-t-butyl-4-hydroxybenzoic acid, MP=205°–208° C.

PREPARATION V

Obtainment of BG2 by Reaction Mechanism B

The recombined organic phases obtained with the procedure of Preparation IVa are agitated with 5 ml of sodium bisulfite. They are washed successively with water (20 ml), sodium bicarbonate (5 ml), and again with water (2×20 ml). After drying over $MgSO_4$, the solvents are evaporated under a vacuum and the evaporation residue is purified on a silica gel column using a diethyl ether/petroleum ether 20/80 v/v mixture as eluent. One obtains 3.29 g (yield: 65.3%) of the expected product, 3,5-di-t-butyl-4-hydroxyphenyl methanol.

PREPARATION VI

Obtainment of BG4 by Reaction Mechanism C

A balloon flask equipped with a spherical funnel for the introduction of liquid reagent ("spherical dropping funnel") and a cooler is placed in a water/ice bath, and filled with an aqueous acid solution of $H_2SO_4$ prepared by using 40 ml of water and 6.5 g of concentrated $H_2SO_4$. When the temperature of this solution drops to 15° C., while stirring 7.5 g (32 mmol) of 3,5-di-t-butyl-4-hydroxybenzaldehyde are added, followed by 3.6 g (23 mmol) of $KMnO_4$ in small portions. The addition of $KMnO_4$ is performed in such a manner that in the course of this addition, the temperature of the reaction medium does not exceed 20° C. Once the addition of $KMnO_4$ is completed, agitation is continued for 6 hours at a temperature below 20° C.

Then drop by drop, an aqueous sodium bisulfite solution is added to dissolve the formed $MnO_2$ (disappearance of dark brown coloring). The remaining precipitate is filtered, washed with water until neutral, and solubilized in 20 ml of an aqueous NaOH solution at 20% weight/volume. The aqueous solution constituting the filtrate is washed with ether, then acidified with HCl (diluted to a third). A new precipitate is formed, which is gathered, washed with water until neutral, dried in the oven at 75° C., then purified on a silica gel column using a diethyl ether/petroleum ether 30/70 volume/volume mixture as eluent. One obtains 4.67 g (yield: 58.3%) of the expected product, 3,5-di-t-butyl-4-hydroxybenzoic acid, MP=205°14 208° C.

PREPARATION VII

Obtainment of BG1 by Reaction Mechanism A 10 mmol of 2,4-di-t-butyl-4-bromophenol (alternative nomenclature: 3,5-di-t-butyl-4-hydroxy-bromobenzene) are reacted with 17 mmol of methanol in an appropriate solvent (notably tetrahydrofuran) in the presence of NaOH. One obtains (yield: 62%) the expected product, 3,5-di-t-butyl-4-hydroxyanisole.

PREPARATION VIII

Obtainment of BG3 by Reaction Mechanism A

By proceeding as indicated in the procedure of Preparation VII above, starting with 10 mmol of 3,5-di-t-butyl-4-trimethylsilyloxy-bromobenzene and 15 mmol of HCHO (in the protected form of $H_2C(OCH_3)_2$), one obtains (yield: 45%) 3,5-di-t-butyl-4-trimethylsilyloxy-benzaldehyde, followed by the expected product, 3,5-di-t-butyl-4-hydroxy-benzaldehyde.

II. Therapeutic use of the compounds having Formula I in which R is an alkyl group with $C_1$-$C_{12}$, an alkenyl group with $C_2$-$C_{12}$, an alkynyl group with $C_2$-$C_{12}$, an alkoxy group with $C_1$-$C_{12}$, a formyl group, an alkanoyl group with $C_2$-$C_{12}$, a hydroxyalkyl group with $C_1$-$C_{12}$, a COOH group, or an A—COOH group where A is an aliphatic hydrocarbon residue with $C_1$-$C_{11}$, and their corresponding salts and esters when R is COH [sic] or A—COOH, for the obtainment of an anti-papillomaviral medication.

These compounds having Formula I are active against papillomaviruses and are useful as anti-papillomaviral agents in the treatment of condylomas due to HPV.

Their anti-papillomaviral activity is improved when they are associated with propolis (Prp). It has in fact been discovered that the synergism of the BHT/Prp association, already disclosed with respect to LCVs such as $HSV_1$, $HSV_2$ and $HSV_1R$, with a BHT-to-Prp ratio by weight of between 100:1 and 650:1 in accordance with the aforementioned French Patent Application No. 90 03 093, is likewise applicable to the association of a compound having Formula I and Prp, with respect to papillomaviruses and notably HPV, and in particular in the treatment of condylomas due to HPV.

In brief, in the organism, the compounds having Formula I and their synergetic associations with Prp intervene as virustatic or virucidal agents, depending on the employed dose, and manifest anti-tumor properties.

BEST METHOD

In accordance with the best method of implementing the invention, for the treatment of lesions of the ano-genital mucosa constituted by acuminate or flat condylomas caused by HPVs, one of the following compounds will be employed: BG1, BG2, BG4, HG1, HG4, HGt4, HG6 or HGt8, if applicable in association with Prp.

The compounds preferred under the invention are BG4 and HG1.

POSOLOGY

The posology recommended for the treatment of ano-genital condylomas caused by HPVs consists in administering at the level of lesions of the ano-genital mucosa a local (i.e., dermatological) composition containing from 5 to 25% by weight of at least one compound having Formula I.

In a practical manner, a local composition will be used containing:

(a) 20% by weight of HG1, (b) Propolis, and 10% by weight of HG1, with an HG1-to-Prp $R_p$ of between 135:1 and 560:1

(c) 10% by weight of BG4, or (d) Propolis and 5–7% of BG4, with a BG4-to-Prp $R_p$ of between 135:1 and 560:1.

Other advantages and characteristics of the invention will be better understood from a reading below of sample preparations and comparative trials.

It is understood that the combination of these elements is by no means limiting but is given simply as an illustration.

I. COMPARATIVE TRIALS

Below, comparative clinical trials are summarized, conducted by the double-blind method on patients of both sexes, age 18 or over, and divided into five groups:

Control group receiving only a dermatological preparation consisting of excipients in the form of a salve;

Group A, receiving the dermatological preparation of the control group into which the product HG1 had been incorporated in a concentration of 20% by weight;

Group B, receiving the dermatological preparation of the control group into which the product HG1 had been incorporated in a concentration of 10% by weight;

Group C, receiving the dermatological preparation of the control group into which an HG1/Prp mixture (with an $R_p$ of 270:1) had been incorporated, with the concentration of HG1 in this dermatological preparation being 10% by weight;

Group D, receiving the dermatological preparation of the control group into which the product BG4 had been incorporated in a concentration of 10% by weight.

The patients, all volunteers, all presented vegetative or papular ano-genital condylomas, and had not received any anti-HPV treatment for at least 15 days prior to the start of the present experiment. Most of the patients were men presenting primarily lesions localized on the membrum virile (notably the sheath). There were as many patients with papular lesions as with vegetative lesions. Approximately one-third of the patients presented 1 or 2 condylomas (i.e., lesions); one-third presented 3 to 5 condylomas and one-third presented at least 6 condylomas. In two out of three cases, these were recidivisms; the patients presenting recidivism had been treated previously with liquid nitrogen, $CO_2$ lasers, podophyllin or podophyllotoxin.

Each patient in the control group and groups A, B, C and D received two daily local applications at the level of the lesions for 14 days. The number of lesions before and after treatment was noted in order to assess the efficacy of treatment.

The demographic and clinical information on the patients in the control group and groups A, B, C and D before treatment appear in Table IV below. The evolution of the number of lesions per group is contained in Table V below.

TABLE IV

| DEMOGRAPHIC AND CLINICAL DATA OF PATIENTS BEFORE TREATMENT | | | | | |
|---|---|---|---|---|---|
| | Control Group | Group A | Group B | Group C | Group D |
| No. of patients | 14 | 14 | 13 | 15 | 14 |
| Male | 11 | 12 | 13 | 12 | 11 |
| Female | 3 | 2 | 0 | 3 | 3 |
| Mean age (years) | 27,9 | 27,7 | 29,3 | 28,2 | 29,4 |
| Location of lesions (1) | | | | | |
| Penis | 10 | 12 | 13 | 12 | 12 |
| Vulva | 2 | 2 | 0 | 3 | 3 |
| Anus | 3 | 0 | 1 | 2 | 1 |

TABLE IV-continued

DEMOGRAPHIC AND CLINICAL DATA OF PATIENTS BEFORE TREATMENT

|  | Control Group | Group A | Group B | Group C | Group D |
|---|---|---|---|---|---|
| Type of condyloma Acominate/flat | 7/7 | 6/8 | 8/5 | 8/7 | 7/7 |
| No. of lesions |  |  |  |  |  |
| 1 or 2 | 4 | 4 | 4 | 6 | 4 |
| 3 to 5 | 3 | 4 | 6 | 6 | 4 |
| 6 or more | 7 | 4 | 3 | 3 | 6 |

TABLE V

EVOLUTION OF NUMBER OF LESIONS AFTER 14 DAYS OF TREATMENT

| No. of lesions | Control Group | Group A | Group B | Group C | Group D |
|---|---|---|---|---|---|
| a) Failure | 12 | 2 | 6 | 2 | 1 |
| of which: |  |  |  |  |  |
| Increase | 4 | 0 | 0 | 0 | 0 |
| Stable | 8 | 2 | 6 | 2 | 1 |
| b) Success | 2 | 12 | 7 | 13 | 13 |
| of which: |  |  |  |  |  |
| Decrease | 2 | 8 | 6 | 7 | 6 |
| Recovery | 0 | 4 | 1 | 6 | 7 |

It was found that the products of the invention, used in Groups A, B, C and D, were well tolerated (only two cases of irritation were observed, and only in Group A who received the local composition containing 20% by weight of HG1), and effective in a statistically significant manner compared to the control group. Among Groups A, B and C receiving HG1 (at 20%, 10% and 10% in association with Prp), it was found that HG1 at a dose of 20% (Group A) is more effective than at a dose of 10% (Group B), and that the HG1/Prp association in which HG1 is present in a dose of 10% (Group C) is at least as effective as or even more effective than HG1 in a dose of 20% (Group A), on the one hand, and better tolerated (absence of irritation) than HG1 in a dose of 20% (Group A), on the other hand.

It was also found that BG4 in a dose of 10% by weight (Group D) is at least as effective as the HG1/Prp association (Group C).

II. SUPPLEMENTARY TESTS

The patients in the control group of the above comparative trials were treated as indicated above with a composition consisting of the dermatological preparation of excipients from tests I above, containing a BG4/Prp association with an $R_p$ of 270:1, and with BG4 being present in a concentration of 5% by weight.

The obtained results were similar or superior to those for Group D in Tests I above.

III. FORMULATION WITH HG1

4 g of polyethylene glycol 1500 stearate are mixed with 12 g of glycerol monostearate, 3 g of glycerol monooleate, 10 g of decyl oleate, 5 g of capric/caprylic triglyceride, and 5 g of glycerol isostearate. The mixture is gradually heated to 70°–75° C. and heating is stopped as soon as the mixture becomes homogeneous. Then 20 g of HG1 are added and the mixture is slowly agitated. Then 3 g of propylene glycol and 38 g of water are poured into the resulting mixture. The resulting mixture is agitated while being allowed to cool to RT. After passing through a homogenizer, it yields a water-in-oil emulsion having the consistency of a cream.

IV. FORMULATION WITH HG1

4 g of polyethylene glycol 1500 stearate are mixed with 12 g of glycerol monostearate, 3 g of glycerol monooleate, 10.3 g of decyl oleate, 5 g of capric/caprylic triglyceride, and 5 g of glycerol isostearate. The mixture is gradually heated to 70°–75° C. and heating is stopped as soon as the mixture becomes homogeneous. Then 10 g of HG1 are added and the mixture is slowly agitated. Then 3 g of propylene glycol and 47 g of water are poured into the resulting mixture. The resulting mixture is agitated while being allowed to cool to RT. After passing through a homogenizer, it yields a water-in-oil emulsion having the consistency of a cream.

V. FORMULATION WITH BG4

4.7 g of polyethylene glycol 1500 stearate are mixed with 12 g of glycerol monostearate, 3 g of glycerol monooleate, 10.3 g of decyl oleate, 5 g of capric/caprylic triglyceride, and 5 g of glycerol isostearate. The mixture is gradually heated to 70°–75° C. and heating is stopped as soon as the mixture becomes homogeneous. Then 10 g of BG4 are added and the mixture is slowly agitated. Then 3 g of propylene glycol and 47 g of water are poured into the resulting mixture. The resulting mixture is agitated while being allowed to cool to RT. After passing through a homogenizer, it yields a water-in-oil emulsion having the consistency of a cream.

VI. FORMULATION WITH HGt4 AND Prp 4.66 g of polyethylene glycol 1500 stearate are mixed with 12 g of glycerol monostearate, 3 g of glycerol monooleate, 10 g of decyl oleate, 5 g of capric/caprylic triglyceride, and 5 g of glycerol isostearate. The mixture is gradually heated to 70°– 75° C. and heating is stopped as soon as the mixture becomes homogeneous. Then 10 g of HGt4 are added and the mixture is slowly agitated. Then 3 g of propylene glycol, 0.3 g of citral, 0.04 g of Prp ($R_p$=250:1) and 47 g of water are poured into the resulting mixture. The resulting mixture is agitated while being allowed to cool to RT. After passing through a homogenizer, it yields a water-in-oil emulsion having the consistency of a cream.

VII. FORMULATION WITH HG1 AND Prp 4.66 g of polyethylene glycol 1500 stearate are mixed with 12 g of glycerol monostearate, 3 g of glycerol monooleate, 10 g of decyl oleate, 5.8 g of capric/caprylic triglyceride, and 5 g of glycerol isostearate. The mixture is gradually heated to 70°–75° C. and heating is stopped as soon as the mixture becomes homogeneous. Then 10 g of HG1 are added and the mixture is slowly agitated. Then 3 g of propylene glycol, 0.04 g of Prp ($R_p$=250:1) and 47 g of water are poured into the resulting mixture. The resulting mixture is agitated while being allowed to cool to RT. After passing through a homogenizer, it yields a water-in-oil emulsion having the consistency of a cream.

I claim:

1. An antiviral composition comprising a substituted phenol selected from the group consisting of:

(a) phenols having the formula

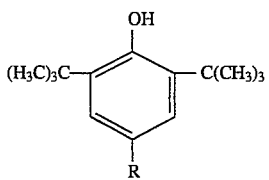

where R is CH$_2$OH, CHO, or COOH, and (b) their corresponding salts and alkyl esters thereof where alkyl is C1–C5 when R is COOH [or A—COOH], wherein the phenol is in an effective antiviral amount, and a physiologically acceptable excipient.

2. The antiviral composition of claim 1, wherein R is selected from the group consisting of CH$_2$OH, CHO and COOH.

3. The antiviral composition of claim 2, wherein the substituted phenol is 3,5-di-t-butyl-4-hydroxybenzoic acid.

4. The antiviral composition of claim 2, wherein the substituted phenol is 3,5-di-t-butyl-4-hydroxyphenylmethanol.

5. The antiviral composition of claim 2, wherein the substituted phenol is 3,5-di-t-butyl-4-hydroxybenzaldehyde.

6. A method for treating diseases caused by lipid-capsid viruses in humans or animals in need of such treatment comprising administering an effective amount of a substituted phenol selected from the group consisting of:

(a) phenols having the formula

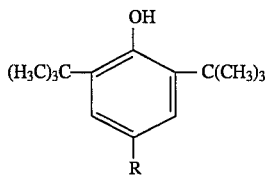

where R is CH$_2$OH, CHO, COOH, and (b) the corresponding salts and alkyl esters thereof where alkyl is C1–C5 when R is COOH [or A—COOH], and a physiologically acceptable excipient.

7. A method for treating diseases caused by herpes viruses in humans or animals in need of such treatment comprising administering an effective amount of a substituted phenol selected from the group consisting of:

(a) phenols having the formula

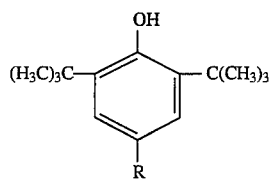

where R is CH$_2$OH, CHO, COOH, and (b) the corresponding salts and alkyl esters thereof where alkyl is C1–C5 when R is COOH [or A—COOH], and a physiologically acceptable excipient.

8. A method for treating diseases caused by papillomaviruses in humans or animals in need of such treatment comprising administering an effective amount of a substituted phenol selected from the group consisting of:

(a) phenols having the formula

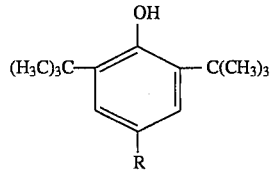

where R is CH$_2$OH, CHO, or COOH, and (b) their corresponding salts and alkyl esters thereof where alkyl is C1–C5 when R is COOH [or A—COOH], and a physiologically acceptable excipient.

9. The method of claim 8 wherein the disease is anogenital condylomas.

10. The method of claim 9 wherein R is COOH.

11. The composition of claim 1, wherein the composition further comprises propolis.

12. The composition of claim 1 wherein the amount of phenol is 5% to 25% of the composition by weight.

13. The composition of claim 12 wherein the amount of phenol is 5% to 10% of the composition by weight.

14. The composition of claim 1 wherein R is COOH or the alkyl ester thereof wherein alkyl is C1–C5.

15. The composition of claim 1 wherein R is CH$_2$OH or COOH, or the corresponding salts and alkyl esters thereof where alkyl is C1–C5 when R is COOH.

16. The composition of claim 1 wherein R is CH$_2$OH or COOH.

* * * * *